US012622854B2

(12) United States Patent
Barfoot et al.

(10) Patent No.: US 12,622,854 B2
(45) Date of Patent: May 12, 2026

(54) HAIR CONDITIONING COMPOSITION FOR IMPROVED DEPOSITION

(71) Applicant: Conopco, Inc., Englewood Cliffs, NJ (US)

(72) Inventors: Richard Jonathan Barfoot, Chesterfield (GB); Michael James Cooke, Wirral (GB); Cesar Ernesto Mendoza Fernandez, Liverpool (GB); Paul Damien Price, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 956 days.

(21) Appl. No.: 17/289,036

(22) PCT Filed: Nov. 28, 2019

(86) PCT No.: PCT/EP2019/082825
§ 371 (c)(1),
(2) Date: Apr. 27, 2021

(87) PCT Pub. No.: WO2020/126377
PCT Pub. Date: Jun. 25, 2020

(65) Prior Publication Data

US 2022/0000736 A1 Jan. 6, 2022

(30) Foreign Application Priority Data

Dec. 19, 2018 (EP) .................................... 18214090

(51) Int. Cl.

| | |
|---|---|
| ***A61K 8/41*** | (2006.01) |
| ***A61K 8/42*** | (2006.01) |
| ***A61K 8/891*** | (2006.01) |
| ***A61Q 5/12*** | (2006.01) |

(52) U.S. Cl.
CPC ................ *A61K 8/416* (2013.01); *A61K 8/42* (2013.01); *A61K 8/891* (2013.01); *A61Q 5/12* (2013.01); *A61K 2800/5426* (2013.01)

(58) Field of Classification Search
None
See application file for complete search history.

(56) References Cited

U.S. PATENT DOCUMENTS

| | | | | |
|---|---|---|---|---|
| 2,131,137 A * | 9/1938 | Ehrhart | C11D 1/00 8/142 |
| 2,580,411 A | 1/1952 | Cusic | |
| 5,374,421 A | 12/1994 | Tashiro et al. | |
| 5,851,982 A * | 12/1998 | Sakata | C07C 229/12 554/114 |
| 6,174,523 B1 | 1/2001 | Morita et al. | |
| 2003/0095944 A1 | 5/2003 | Midha | |
| 2003/0108507 A1 | 6/2003 | Clipson et al. | |
| 2005/0175569 A1 | 8/2005 | Fack | |
| 2006/0140900 A1 | 6/2006 | Watanabe et al. | |
| 2007/0104672 A1* | 5/2007 | Decoster | A61K 8/4993 424/70.28 |
| 2008/0160093 A1* | 7/2008 | Schwartz | A61P 31/10 424/642 |
| 2012/0148644 A1 | 6/2012 | Popplewell et al. | |
| 2013/0330292 A1 | 12/2013 | Lei et al. | |
| 2014/0246041 A1 | 9/2014 | Krueger | |
| 2015/0150763 A1 | 6/2015 | Casugbo et al. | |
| 2017/0087074 A1 | 3/2017 | Perusse et al. | |
| 2017/0087077 A1 | 3/2017 | Perusse et al. | |

FOREIGN PATENT DOCUMENTS

| | | |
|---|---|---|
| CN | 1561194 | 1/2005 |
| CN | 1568174 | 1/2005 |
| CN | 104507451 | 4/2015 |
| DE | 10042374 | 3/2002 |
| EP | 0530974 | 3/1993 |
| EP | 1016650 | 3/2003 |
| JP | 08198828 | 8/1996 |

(Continued)

OTHER PUBLICATIONS

JP-08231478-A Eng Tran. Published: Sep. 10, 1996.*
MoKnowsHair. https://moknowshair.com/heatprotectants/. Published: Sep. 16, 2013.*
Dimethicone.https://cvskinlabs.com/dimethicone-the-truth-behind-this-common-cosmetics-ingredient/. Published: Apr. 16, 2012.*
JP3502680 Eng Tran. Published: Mar. 2, 2004.*
Search Report and Written Opinion EP18214094; Jun. 28, 2019.
Search Report and Written Opinion in EP18214093; Jun. 28, 2019.
Search Report and Written Opinion in EP18214090; Jul. 10, 2019.
Search Report and Written Opinion in PCTEP2019084380; Feb. 17, 2020.
Search Report and Written Opinion in PCTEP2019082825; May 12, 2020.

(Continued)

*Primary Examiner* — David J Blanchard
*Assistant Examiner* — Lori K Mattison
(74) *Attorney, Agent, or Firm* — Carter, DeLuca & Farrell, LLP; George Likourezos; Bret P. Shapiro

(57) ABSTRACT

A hair conditioning composition for improved deposition of benefit agents including a linear cationic conditioning surfactant, a linear fatty material, a particulate benefit agent, and a branched cationic co-surfactant. The composition includes 0.01 to 10 wt % of the linear, cationic conditioning surfactant, 0.1 to 10 wt % of the linear fatty material, and 0.01 to 5 wt %, at 100% active, of the branched cationic co-surfactant. The molar ratios of branched cationic co-surfactants to linear cationic conditioning surfactants are in the range of from 1:20 to 1:1.

Structure 1

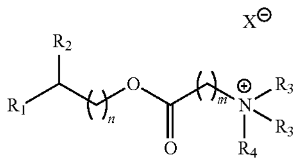

16 Claims, No Drawings

(56) References Cited

FOREIGN PATENT DOCUMENTS

| | | | | | |
|---|---|---|---|---|---|
| JP | H08198828 | | | 8/1996 | |
| JP | 08231478 | A | * | 9/1996 | ............... A61K 7/06 |
| JP | H11228358 | A | | 8/1999 | |
| JP | 3502680 | | | 3/2004 | |
| JP | 2005060271 | | | 3/2005 | |
| JP | 2006206585 | A | | 8/2006 | |
| JP | 2009108057 | | | 5/2009 | |
| JP | 2015522638 | A | | 8/2015 | |
| JP | 2021524160 | A | | 9/2021 | |
| JP | 2021535072 | A | | 12/2021 | |
| WO | WO0143718 | | | 6/2001 | |
| WO | WO02102334 | | | 12/2002 | |
| WO | WO2009016555 | | | 2/2009 | |
| WO | WO2013083349 | | | 6/2013 | |
| WO | 2014016350 | A1 | | 1/2014 | |
| WO | WO2014016351 | | | 1/2014 | |
| WO | WO2014016352 | | | 1/2014 | |
| WO | WO2014016353 | | | 1/2014 | |
| WO | WO2014016354 | | | 1/2014 | |
| WO | WO2017211701 | | | 12/2017 | |
| WO | 2019222696 | A1 | | 11/2019 | |
| WO | 2020033384 | A1 | | 2/2020 | |

OTHER PUBLICATIONS

Search Report and Written Opinion in PCTEP2019084382; Feb. 17, 2020.

IPRP in PCTEP2019084380; Jul. 1, 2021; World Intellectual Property Org. (WIPO).

IPRP1 in PCTEP2019084382; Jul. 1, 2021; World Intellectual Property Org. (WIPO).

IPRP1 in PCTEP2019082825; Jul. 1, 2021; World Intellectual Property Org. (WIPO).

* cited by examiner

HAIR CONDITIONING COMPOSITION FOR IMPROVED DEPOSITION

CROSS-REFERENCE TO RELATED APPLICATIONS

This application is a U.S. 371 National Stage Application of PCT International Application No. PCT/EP2019/082825, with international filing date of Nov. 28, 2019, which claims the benefit of and priority to European patent application No. 18214090.5 filed Dec. 19, 2018, the contents of which are incorporated herein by reference in their entireties.

FIELD OF THE INVENTION

The invention is concerned with conditioning compositions, containing a branched co-surfactant, for the treatment of hair, which comprise a benefit agent, for example silicone, to be deposited onto the hair during use and particularly relates to a conditioning composition that enables increased amounts of benefit agent to be deposited.

BACKGROUND AND PRIOR ART

In personal care compositions, such as hair treatment compositions, the deposition and delivery of benefit agents are often key drivers of product performance. For example, many of the hair conditioner products in the market today work to deliver benefits to hair by depositing benefit agents such as fragrance materials, silicones and damage repair actives onto the hair during the wash and care process.

However, consumers report being disappointed by the level of benefit derived from use of some compositions. This is usually caused by insufficient amount of benefit agents being delivered to the surface. It is, therefore, desirable to develop compositions that provide improved delivery of benefit materials to a surface, for example hair.

Glycine betaine derivatives are known in home and personal care products. These derivatives have been used in hair applications to deliver conditioning benefits to hair.

US 2017/087074 (Centre National De La Recherche Scientifique) discloses surfactant compositions for use in cosmetic and pharmaceutical compositions. The compositions include an alkylpolyglucoside grafted with glycine betaine in combination with a glycine betaine and are stable. Similar compositions are disclosed in US 2017/087077.

US 2014/246041 (Henkel) discloses a composition for conditioning hair containing a defined esterquat which has a structure that can cover the glycine betaines and at least one care-providing substance(s) selected from the group of L-carnitine and/or salts thereof, and/or taurine and/or salts thereof, and/or vitamins and vitamin precursors, and/or niacinamide, and/or ubiquinone, and/or ectoin. WO 13/083349 discloses a similar esterquat for conditioning keratin fibres.

EP 1 016650 (Kao) disclose a method of preparation of a betaine alkyl ester which can be used in hair cosmetics to give feel benefits to hair. Cetanol (ex Kao Corporation) is used in the formulation examples.

US2015/0150763 discloses specific conditioning compositions comprising droplets of silicone conditioning agent that enable increased silicone deposition onto hair.

Product rheology is a key attribute to consumers. We have, however, found that adding branched surfactant materials into gel networks disrupts the gel bilayers and consequently reduces viscosity and yield stress to unacceptably low levels.

Despite the prior art, there remains a need to deliver improved delivery of benefits to hair without compromising on consumer desired viscosity characteristics.

We have now surprisingly found that the selection of branched glycine betaine materials in combination with a linear cationic surfactant results in an unexpectedly big enhancement in the deposition of benefit agent whilst maintaining excellent product rheology.

All percentages quoted herein are by weight based on total weight, unless otherwise stated.

DEFINITION OF THE INVENTION

Accordingly, there is provided a composition comprising:

(i) 0.01 to 10 wt % of a linear, cationic conditioning surfactant;

(ii) 0.1 to 10 wt % of a linear fatty material;

(iii) a particulate benefit agent;

(iv) 0.01 to 5 wt %, at 100% active, of a branched cationic co-surfactant, selected from structure 1—

Structure 1

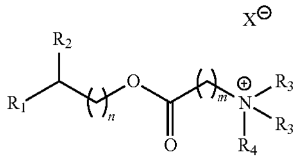

wherein:

$R_1$, and $R_2$ comprise linear alkyl chains, saturated or unsaturated, with carbon-carbon chain lengths of from $C_4$ to $C_{20}$, preferably from $C_6$ to $C_{18}$; more preferably from $C_8$ to $C_{12}$, most preferably from $C_6$ to $C_{10}$, n has a range of from 0 to 10, preferably selected from 0 and 1;

m has a range of from 1 to 6, preferably selected from 1 and 2;

$R_3$ comprises an alkyl chain having a carbon-carbon chain length of from $C_1$ to $C_4$, preferably $C_1$ to $C_2$;

$R_4$ comprises a proton or an alkyl chain having a carbon-carbon chain length of from $C_1$ to $C_4$, preferably $C_1$ to $C_2$; and X is an organic or inorganic anion;

wherein the molar ratios of branched cationic co-surfactants (iv) to linear cationic surfactants (i) are in the range of from 1:20 to 1:1, preferably from 1:10 to 1:1, most preferably 1:5 to 1:2.

In a second aspect, the invention provides a method of increasing benefit agent deposition to hair comprising the step of applying to hair a composition of the first aspect, compared to the same composition without a branched cationic cosurfactant in accordance with structure 1. The method of the invention preferably comprises an additional step of rinsing the composition from the hair.

Preferably, the method is a method of increasing silicone deposition to hair comprising the steps of applying to hair a composition as defined by the first aspect of the invention and rinsing the hair with water, wherein the particulate benefit agent is silicone.

Compositions in accordance with the invention are preferably formulated as conditioners for the treatment of hair (typically after shampooing) and subsequent rinsing.

General Description of the Invention

Preferably, the treatment composition is selected from a rinse-off hair conditioner, a hair mask, a leave-on conditioner composition, and a pre-treatment composition, more preferably selected from a rinse-off hair conditioner, a hair mask, a leave-on conditioner composition, and a pre-treatment composition, for example an oil treatment, and most preferably selected from a rinse-off hair conditioner, a hair mask and a leave-on conditioner composition. The treatment composition is preferably selected from a rinse-off hair conditioner and a leave-on conditioner.

Rinse off conditioners for use in the invention are conditioners that are typically left on wet hair for 1 to 2 minutes before being rinsed off.

Hair masks for use in the present invention are treatments that are typically left on the hair for 3 to 10 minutes, preferably from 3 to 5 minutes, more preferably 4 to 5 minutes, before being rinsed off.

Leave-on conditioners for use in the invention are typically applied to the hair and left on the hair for more than 10 minutes, and preferably are applied to the hair after washing and not rinsed out until the next wash.

The Linear Cationic Conditioning Surfactant

Conditioner compositions will comprise a linear cationic conditioning surfactant, which is cosmetically acceptable and suitable for topical application to the hair.

Preferably, the linear cationic conditioning surfactants have the formula 1: $N^+(R^1)(R^2)(R^3)(R^4)$, wherein $R^1$, $R^2$, $R^3$ and $R^4$ are independently ($C_1$ to $C_6$) alkyl or benzyl.

In formula 1, preferably, one, two or three of $R^1$, $R^2$, $R^3$ and $R^4$ are independently ($C_4$ to $C_{30}$) alkyl and the other $R^1$, $R^2$, $R^3$ and $R^4$ group or groups are ($C_1$-$C_6$) alkyl or benzyl.

More preferably, one or two of $R^1$, $R^2$, $R^3$ and $R^4$ are independently ($C_6$ to $C_{30}$) alkyl and the other $R^1$, $R^2$, $R^3$ and $R^4$ groups are ($C_1$-$C_6$) alkyl or benzyl groups. Optionally, the alkyl groups may comprise one or more ester (—OCO— or —COO—) and/or ether (—O—) linkages within the alkyl chain. Alkyl groups may optionally be substituted with one or more hydroxyl groups. Alkyl groups may be straight chain or branched and, for alkyl groups having 3 or more carbon atoms, cyclic. The alkyl groups may be saturated or may contain one or more carbon-carbon double bonds (e.g., (oleyl). Alkyl groups are optionally ethoxylated on the alkyl chain with one or more ethyleneoxy groups.

Suitable quaternary amine salts for use in conditioner compositions according to the invention are quaternary amine salt comprising from 12 to 24 carbon atoms, preferably from 16 to 22 carbon atoms.

Suitable quaternary amine salts for use in conditioner compositions according to the invention include cetyltrimethylammonium chloride, behenyltrimethylammonium chloride, Behentrimonium methosulphate, BehenylAmido Propyl Di-Methyl Amine, cetyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, Stearalkonium Chloride, Stearalkonium methosulphate, didodecyldimethylammonium chloride, dioctadecyldimethylammonium chloride, tallowtrimethylammonium chloride, dihydrogenated tallow dimethyl ammonium chloride (e.g., Arquad 2HT/75 from Akzo Nobel) and cocotrimethylammonium chloride.

Preferred quaternary amine salts selected from behenyltrimethylammonium chloride, Behentrimonium methosulphate, cetyltrimethylammonium chloride, and mixtures thereof.

A particularly useful cationic surfactant for use in conditioners according to the invention is cetyltrimethylammonium chloride, available commercially, for example as GENAMIN CTAC, ex Hoechst Celanese. Another particularly preferred cationic surfactant for use in conditioners according to the invention is behenyltrimethylammonium chloride, available commercially, for example as GENAMIN KDMP, ex Clariant.

Further suitable cationic surfactants include those materials having the CTFA designations Quaternium-5, Quaternium-31, and Quaternium-18. Mixtures of any of the foregoing materials may also be suitable.

Another example of a class of suitable cationic surfactants for use in the invention, either alone or together with one or more other cationic surfactants, is a combination of (i) and (ii) below:

(i) an amidoamine corresponding to the general formula (II):

$$R^1CONH(CH_2)_mN(R^2)R^3 (II)$$

in which $R^1$ is a hydrocarbyl chain having 10 or more carbon atoms, $R^2$ and $R^3$ are independently selected from hydrocarbyl chains of from 1 to 10 carbon atoms, and m is an integer from 1 to about 10; and (ii) an acid.

As used herein, the term hydrocarbyl chain means an alkyl or alkenyl chain.

Preferred amidoamine compounds are those corresponding to formula (II) in which $R^1$ is a hydrocarbyl residue having from about 11 to about 24 carbon atoms, $R^2$ and $R^3$ are each independently hydrocarbyl residues, preferably alkyl groups, having from 1 to about 4 carbon atoms, and m is an integer from 1 to about 4.

Preferably, $R^2$ and $R^3$ are methyl or ethyl groups.

Preferably, m is 2 or 3, i.e. an ethylene or propylene group.

Preferred amidoamines useful herein include stearamidopropyldimethylamine, stearamidopropyldiethylamine, stearamidoethyldiethylamine, stearamidoethyldimethylamine, palmitamidopropyldimethylamine, palmitamidopropyl-diethylamine, palmitamidoethyldiethylamine, palmitamidoethyldimethylamine, behenamidopropyldimethyl-amine, behenamidopropyldiethylmine, behenamidoethyldiethylamine, behenamidoethyldimethylamine, arachidamidopropyl-dimethylamine, arachidamidopropyldiethylamine, arachid-amidoethyldiethylamine, arachidamidoethyldimethylamine, and mixtures thereof. Particularly preferred amidoamines useful herein are stearamidopropyldimethylamine, stearamidoethyldiethylamine, and mixtures thereof.

Commercially available amidoamines useful herein include:

stearamidopropyldimethylamine with tradenames LEXAMINE S-13 available from Inolex (Philadelphia Pennsylvania, USA) and AMIDOAMINE MSP available from Nikko (Tokyo, Japan), stearamidoethyldiethylamine with a tradename AMIDOAMINE S available from Nikko, behenamidopropyldimethylamine with a tradename INCROMINE BB available from Croda (North Humberside, England), and various amidoamines with tradenames SCHERCODINE series available from Scher (Clifton New Jersey, USA).

Acid may be any organic or mineral acid which is capable of protonating the amidoamine in the conditioner composition. Suitable acids useful herein include hydrochloric acid, acetic acid, tartaric acid, fumaric acid, lactic acid, malic acid, succinic acid, and mixtures thereof. Preferably, the acid is selected from the group consisting of acetic acid, tartaric acid, hydrochloric acid, fumaric acid, lactic acid and mixtures thereof.

The primary role of the acid is to protonate the amidoamine in the hair treatment composition thus forming a tertiary amine salt (TAS) in situ in the hair treatment composition. The TAS in effect is a non-permanent quaternary ammonium or pseudo-quaternary ammonium cationic surfactant.

Suitably, the acid is included in a sufficient amount to protonate more than 95 mole % (293 K) of the amidoamine present.

In conditioners for use in the invention, the level of linear cationic conditioning surfactant will generally range from 0.01 to 10%, more preferably 0.05 to 7.5%, most preferably 0.1 to 5% by total weight of cationic conditioning surfactant based on the total weight of the composition.

The Linear Fatty Material

The composition of the invention comprises from 0.1 to 10 wt % of a linear fatty material.

The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof. Preferably the linear fatty material is selected from a fatty alcohol and a fatty acid, most preferably a fatty alcohol.

Preferably, the alkyl chain of the fatty material is fully saturated. Representative fatty materials comprise from 8 to 22 carbon atoms, more preferably 16 to 22.

Suitable fatty alcohols comprise from 8 to 22 carbon atoms, preferably 16 to 22, most preferably 016 to $C_{18}$. Fatty alcohols are typically compounds containing straight chain alkyl groups. Preferably, the alkyl groups are saturated. Examples of preferred fatty alcohols include cetyl alcohol, stearyl alcohol and mixtures thereof. The use of these materials is also advantageous in that they contribute to the overall conditioning properties of compositions for use in the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty material in conditioners of the invention is suitably from 0.01 to 10, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

The Particulate Benefit Agent

The composition of the invention comprises a particulate benefit agent. The particulate benefit agent is preferably selected from conditioning actives, scalp actives, encapsulated fragrance, emulsified fragrance, and mixtures thereof. More preferably the particulate benefit agent is selected from conditioning actives, encapsulated fragrance and mixtures thereof. Most preferably, the particulate benefit agent is selected from a silicone emulsion and an encapsulated fragrance.

Preferred conditioning actives are silicone emulsions.

Silicone

The compositions of the invention can contain, emulsified droplets of a silicone conditioning agent.

Suitable silicones include polydiorganosiloxanes, in particular polydimethylsiloxanes which have the CTFA designation dimethicone. Also suitable for use compositions of the invention are polydimethyl siloxanes having hydroxyl end groups, which have the CTFA designation dimethiconol. Also suitable for use in compositions of the invention are silicone gums having a slight degree of cross-linking, as are described for example in WO 96/31188. Preferably, the silicone is selected from the group consisting of dimethicone, dimethiconol, amodimethicone and mixtures thereof. Also preferred are blends of amino-functionalised silicones with dimethicones.

The viscosity of the emulsified silicone itself (not the emulsion or the final hair conditioning composition) is typically at least 10,000 cst at 25° C. the viscosity of the silicone itself is preferably at least 60,000 cst, most preferably at least 500,000 cst, ideally at least 1,000,000 cst. Preferably the viscosity does not exceed $10^9$ cst for ease of formulation.

Emulsified silicones for use in the compositions of the invention will typically have a D90 silicone droplet size in the composition of less than 30, preferably less than 20, more preferably less than 10 micron, ideally from 0.01 to 1 micron. Silicone emulsions having an average silicone droplet size (D50) of 0.15 micron are generally termed microemulsions.

Silicone particle size may be measured by means of a laser light scattering technique, for example using a 2600D Particle Sizer from Malvern Instruments. Examples of suitable pre-formed emulsions include Xiameter MEM 1785 and microemulsion DC2-1865 available from Dow Corning. These are emulsions/microemulsions of dimethiconol. Cross-linked silicone gums are also available in a pre-emulsified form, which is advantageous for ease of formulation.

A further preferred class of silicones for inclusion in compositions of the invention are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone". A preferred amodimethicone is commercially available from Dow Corning as DC 7134.

Specific examples of amino functional silicones suitable for use in the invention are the aminosilicone oils DC2-8220, DC2-8166 and DC2-8566 (all ex Dow Corning).

Suitable quaternary silicone polymers are described in EP-A-0 530 974. A preferred quaternary silicone polymer is K3474, ex Goldschmidt.

Also suitable are emulsions of amino functional silicone oils with non ionic and/or cationic surfactant.

Pre-formed emulsions of amino functional silicone are also available from suppliers of silicone oils such as Dow Corning and General Electric. Specific examples include DC939 Cationic Emulsion and the non-ionic emulsions DC2-7224, DC2-8467, DC2-8177 and DC2-8154 (all ex Dow Corning).

The total amount of silicone is preferably from 0.1 wt % to 10% wt of the total composition more preferably from 0.1 wt % to 5 wt %, most preferably 0.25 wt % to 3 wt % is a suitable level.

The branched Cationic Co-Surfactant

The composition of the invention comprises a branched cationic co-surfactant.

The branched cationic co-surfactant is preferably present in an amount of from 0.1 wt % to 1 wt %, most preferably 0.1 wt % to 0.5 wt %, by weight of the total composition.

The branched cationic co-surfactant is selected from structure 1

Structure 1

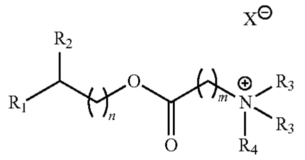

wherein:

$R_1$, and $R_2$ comprise linear alkyl chains, saturated or unsaturated, with carbon-carbon chain lengths of from $C_4$ to $C_{20}$, preferably from $C_6$ to $C_{18}$; more preferably from $C_8$ to $C_{12}$, most preferably from $C_6$ to $C_{10}$ n has a range of from 0 to 10;

m has a range of from 1 to 6;

$R_3$ comprises an alkyl chain having a carbon-carbon chain length of from $C_1$ to $C_4$, preferably $C_1$ to $C_2$;

$R_4$ comprises a proton or an alkyl chain having a carbon-carbon chain length of from $C_1$ to $C_4$, preferably $C_1$ to $C_2$; and X is an organic or inorganic anion;

wherein the molar ratios of branched cationic co-surfactants (iv) to linear cationic surfactants (i) are in the range of from 1:20 to 1:1, preferably from 1:10 to 1:1, most preferably 1:5 to 1:2.

In structure 1, the amine head group is charged within the final formulation. Raw materials include, however, species where the charge is not permanent and can be induced by protonation in the formulation using a strong acid. When $R_4$ is a proton in the above general formulae therefore, the proton may be present in the raw material or become associated during formulation.

The variable, m has a range of from 1 to 6, preferably selected from 1 and 2, most preferably 1.

The variable, n, has a range of from 0 to 10 and is preferably selected from 0 and 1.

Optionally, at least one of $R_1$ and $R_2$ comprise linkages within the alkyl chain selected from the group consisting of an ester group (—OCO— or —COO—), an amido group (—NOC— or NCO—), and an ether group (—O—).

X is an organic or inorganic anion. Preferably, X comprises an anion selected from the halide ions; sulphates of the general formula $RSO_3^-$, wherein R is a saturated or unsaturated alkyl radical having 1 to 4 carbon atoms, and anionic radicals of organic acids.

Preferred halide ions are selected from fluoride, chloride, bromide and iodide. Preferred anionic radicals of organic acids are selected from maleate, fumarate, oxalate, tartrate, citrate, lactate and acetate. Preferred sulphates are methanesulphonate and ethanesulphonate.

Most preferably, $X^-$ comprises an anion selected from a halide, a methanesulfonate group and an ethanesulphonate group.

The branched co-surfactant is present in an amount of from 0.01 to 5 wt %, preferably 0.1 to 1, most preferably 0.1 to 0.5 (at 100% active and based on weight of total composition).

Examples of suitable materials conforming to structure 1 are 2-((2-butyloctyl)oxy)-N,N,N-trimethyl-2-oxoethan-1-aminium methanesulphonate, 2-((2-hexyldecyl)oxy)-N,N,N-trimethyl-2-oxoethan-1-aminium methanesulphonate, N,N,N-trimethyl-2-((2-octyldodecyl)oxy)-2-oxoethan-1-aminium methanesulphonate, 2-((2-decyltetradecyl)oxy)-N,N,N-trimethyl-2-oxoethan-1-aminium methanesulphonate, 2-((2-dodecylhexadecyl)oxy)-N,N,N-trimethyl-2-oxoethan-1-aminium methanesulphonate and N,N,N-trimethyl-2-oxo-2-((2-tetradecyloctadecyl)oxy)ethan-1-aminium methanesulphonate.

Composition Rheology

The compositions of the invention provide good viscosity and yield stress properties. The compositions have a preferred yield stress range of from 30 to 200 Pascals (Pa), most preferably from 40 to 150 Pa peak value at 25° C. and 1 Hz. The method to measure the yield stress uses a serrated parallel-plate geometry, 40 mm in diameter, attached to a suitable rheometer capable of applying oscillations at a constant frequency of 1 Hz, and an amplitude sweep in the range of 0.1% to 2000%. The amplitude sweep range is applied at no more than ten points per decade of strain range covered at no more than 4 cycles per amplitude. The instrument should be operated under controlled strain, such as with the ARES G2 Rheometer from TA Instruments. The geometry's temperature should be set at 25° C. by means of, for example, a Peltier-controlled plate, or a recirculating bath. The yield stress is determined by plotting the elastic stress against strain amplitude, and at the peak of the curve, the maximum value is quoted as the yield stress. The elastic stress is calculated as the multiplication of (storage modulus)*(strain amplitude), each readily obtained from the instrument.

The compositions have a viscosity of from 5,000 to 750,000 centipoise, preferably from 50,000 to 600,000 centipoise, more preferably from 50,000 to 450,000 as measured at 30° C. on a Brookfield RVT using a Spindle A or B at 0.5 rpm for 60 seconds on a Helipath stand.

A preferred conditioner comprises a conditioning gel phase. These conditioners have little or no vesicle content. Such conditioners and methods for making them are described in WO2014/016354, WO2014/016353, WO2012/016352 and WO2014/016351.

Such a conditioning gel phase comprises, by total weight of the composition, i) from 0.4 to 8 wt % of fatty alcohol having from 8 to 22 carbons, ii) from 0.1 to 2 wt % of cationic surfactant, and the composition confers a Draw Mass of from 1 to 250 g, preferably 2 to 100 g, more preferably 2 to 50 g, even more preferably 5 to 40 g and most preferably 5 to 25 g to hair treated with the composition.

Draw Mass is the mass required to draw a hair switch through a comb or brush. Thus the more tangled the hair the greater the mass required to pull the switch through the comb or brush, and the greater the level of condition of the hair, the lower the Draw Mass.

The Draw Mass is the mass required to draw a hair switch, for example of weight 1 to 20 g, length 10 to 30 cm, and width 0.5 to 5 cm through a comb or brush, as measured by first placing the hair switch onto the comb or brush, such that from 5 to 20 cm of hair is left hanging at the glued end of the switch, and then adding weights to the hanging end until the switch falls through the comb or brush.

Preferably, the hair switch is of weight 1 to 20 g, more preferably 2 to 15 g, most preferably from 5 to 10 g. Preferably, the hair switch has a length of from 10 to 40 cm, more preferably from 10 to 30 cm, and a width of from 0.5 to 5 cm, more preferably from 1.5 to 4 cm.

Most preferably, the Draw Mass is the mass required to draw a hair switch, for example of weight 10 g, length 20 cm, and width 3 cm through a comb or brush, as measured by first placing the hair switch onto the comb or brush, such that from 20 cm of hair is left hanging at the glued end of the switch, and then adding weights to the hanging end until the switch falls through the comb or brush.

Further Ingredients

The composition according to the invention may comprise any of a number of ingredients which are common to hair conditioning compositions.

Other ingredients may include deposition polymers viscosity modifiers, preservatives, colouring agents, polyols such as glycerine and polypropylene glycol, chelating agents such as EDTA, antioxidants such as vitamin E acetate, fragrances, antimicrobials and sunscreens. Each of these ingredients will be present in an amount effective to accomplish its purpose. Generally these optional ingredients are included individually at a level of up to about 5% by weight of the total composition.

Preferably, the further ingredients include perfumes, thickeners, preservatives, colours and conditioning silicones.

Mixtures of any of the above active ingredients may also be used.

Generally, such ingredients are included individually at a level of up to 2%, preferably up to 1%, by weight of the total composition.

Embodiments of the invention are given in the following examples, in which all percentages are quoted by weight based on total weight unless otherwise stated.

EXAMPLES

Example 1

Composition 1 in Accordance with the Invention and Comparative Composition A The following compositions were prepared:

TABLE 1

Compositions of example A (comparative) and example 1 (in accordance with the invention).

| Ingredients | Example A Comparative | Example 1 Structure 1 |
|---|---|---|
| Behentrimonium Chloride | 2.00 | 2.00 |
| Cetearyl Alcohol | 4.00 | 4.00 |
| Xiameter MEM-7134 | 1.00 | 1.00 |
| N,N,N-trimethyl-2-((2-octyldodecyl)oxy)-2-oxoethan-1-aminium methanesulphonate | — | 0.50 |
| Parfum | 0.60 | 0.60 |
| Preservative | 0.30 | 0.30 |
| Aqua | to 100 | to 100 |

The conditioners in examples A and 1 were prepared using the following method:

1. Surfactants and fatty materials (including branched materials) are added to a suitable vessel and heated to 80° C.
2. The molten blend is added to suitable amount of water according to the compositions disclosed, at a temperature between 45 and 70° C.
3. Mixture is mixed until opaque and thick.
4. The heat is then turned off, cooled to below 40° C., and the rest of the water is added along with the remaining materials.
5. Finally, the formulation is mixed at high shear on a Silverson mixer at 5000 rpm for 5 minutes.

Example 2

Treatment of Hair with Compositions A and 1

The hair used was dark brown European hair, in switches of 5 g weight and 6 inches in length.

Hair was first treated with a cleansing shampoo using the following method: The hair fibres were held under running water for 30 seconds, shampoo applied at a dose of 0.1 ml of shampoo per 1 g of hair and rubbed into the hair for 30 seconds. Excess lather was removed by holding under running water for 30 seconds and the shampoo stage repeated. The hair was rinsed under running water for 1 minute.

The wet hair was then treated with the compositions using the following method: Conditioner was applied to the wet hair at a dose of 0.2 ml of conditioner per 1 g of hair and massaged into the hair for 1 minute. The hair was rinsed under running water for 1 minute and excess water removed.

Example 3

Silicone Deposition and Yield Stress onto Hair Treated with Compositions A and 1

TABLE 2

Yield stress and amount of silicone deposited on hair treated with Example A (comparative) and example 1 (in accordance with the invention).

| Ingredients | Example A Comparative | Example 1 Structure 1 |
|---|---|---|
| Silicone Deposition [ppm] | 431 | 1,354 |
| Silicone Deposition ST DEV [ppm] | 63 | 309 |
| Yield stress [Pa] (−+10 Pa) | 182 | 167 |

The invention claimed is:

1. A composition comprising:

(i) 0.01 to 10 wt % of a linear, cationic conditioning surfactant;

(ii) 0.1 to 10 wt % of a linear fatty material;

(iii) a particulate benefit agent;

(iv) 0.01 to 5 wt %, at 100% active, of a branched cationic co-surfactant, selected from structure 1

Structure 1

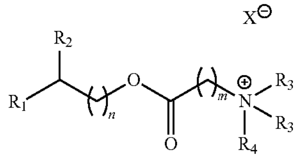

wherein:

$R_1$, and $R_2$ comprise linear alkyl chains, saturated or unsaturated, with carbon-carbon chain lengths of from $C_6$ to $C_{10}$;

n has a range of from 0 to 10;

m has a range of from 1 to 6;

$R_3$ comprises an alkyl chain having a carbon-carbon chain length of from $C_1$ to $C_4$;

$R_4$ is a proton; and

X is a halide;

wherein the molar ratios of branched cationic co-surfactants (iv) to linear cationic conditioning surfactants (i) are in the range of from 1:20 to 1:1.

2. The composition as claimed in claim 1, wherein the linear cationic conditioning surfactant has the formula 1: $N^+(R^1)$ $(R^2)$ $(R^3)$ $(R^4)$, wherein $R^1$, $R^2$, $R^3$ and $R^4$ are independently $C_1$ to $C_{30}$ alkyl or benzyl.

3. The composition as claimed in claim 1, wherein the linear cationic conditioning surfactant is selected from behenyltrimethylammonium chloride, behentrimonium methosulphate, cetyltrimethylammonium chloride, and mixtures thereof.

4. The composition as claimed in claim 1, further comprising an amidoamine corresponding to the general formula (II):

$$R^1CONH(CH_2)_mN(R_2)R_3 \quad (II)$$

in which $R^1$ is a hydrocarbyl chain having 10 or more carbon atoms, $R^2$ and $R^3$ are independently selected from hydrocarbyl chains of from 1 to 10 carbon atoms, and m is an integer from 1 to 10; and an acid.

5. The composition as claimed in claim 1, wherein the branched cationic co-surfactant is present in an amount of from 0.1 wt % to 1 wt %.

6. The composition as claimed in claim 1, wherein the molar ratios of branched cationic co-surfactants (iv) to linear cationic conditioning surfactants (i) are in the range of from 1:10 to 1:1.

7. The composition as claimed in claim 1, wherein the particulate benefit agent is selected from conditioning actives, scalp actives, encapsulated fragrance, emulsified fragrance, and mixtures thereof.

8. The composition as claimed in claim 7, wherein the particulate benefit agent is a silicone.

9. The composition as claimed in claim 8, wherein the silicone is present in an amount of from 0.1 wt % to 10 wt % of the total composition.

10. The composition as claimed in claim 1, which has a yield stress in the range of from 30 to 200 Pascals (Pa) peak value at 25° C. and 1 Hz.

11. The composition as claimed in claim 1 wherein the branched cationic co-surfactant is present in an amount of from 0.1 wt % to 0.5 wt %.

12. The composition as claimed in claim 1 wherein the molar ratios of branched cationic co-surfactants (iv) to linear cationic conditioning surfactants (i) are in the range of from 1:5 to 1:2.

13. The composition as claimed in claim 8, wherein the silicone is present in an amount of from 0.1 wt % to 5 wt %.

14. The composition as claimed in claim 8, wherein the silicone is present in an amount of from 0.25 wt % to 3 wt %.

15. The composition as claimed in claim 1, wherein n is 0 or 1, and m is 1 or 2.

16. The composition as claimed in claim 15, wherein the molar ratios of branched cationic co-surfactants (iv) to linear cationic conditioning surfactants (i) are in the range of from 1:10 to 1:1.

* * * * *